(12) United States Patent
Domenicali et al.

(10) Patent No.: US 7,990,545 B2
(45) Date of Patent: *Aug. 2, 2011

(54) SURFACE MEASUREMENT OF IN-VIVO SUBJECTS USING SPOT PROJECTOR

(75) Inventors: Peter Domenicali, Wilmington, MA (US); Clifford Hoyt, Wellesley, MA (US); Peter Miller, Cambridge, MA (US)

(73) Assignee: Cambridge Research & Instrumentation, Inc., Woburn, MA (US)

( * ) Notice: Subject to any disclaimer, the term of this patent is extended or adjusted under 35 U.S.C. 154(b) by 166 days.

This patent is subject to a terminal disclaimer.

(21) Appl. No.: 12/005,510

(22) Filed: Dec. 27, 2007

(65) Prior Publication Data
US 2008/0198355 A1    Aug. 21, 2008

Related U.S. Application Data

(60) Provisional application No. 60/877,313, filed on Dec. 27, 2006.

(51) Int. Cl.
*G01B 11/24* (2006.01)
(52) U.S. Cl. .......................... 356/601; 356/603; 356/609
(58) Field of Classification Search .......... 356/601–623; 600/473, 476, 431, 410, 310
See application file for complete search history.

(56) References Cited

U.S. PATENT DOCUMENTS

| | | | | |
|---|---|---|---|---|
| 4,743,771 A * | 5/1988 | Sacks et al. | ............... | 250/559.22 |
| 4,900,940 A * | 2/1990 | Nakamura | ............... | 250/559.23 |
| 4,939,574 A * | 7/1990 | Petersen et al. | ................. | 348/89 |
| 5,404,163 A * | 4/1995 | Kubo | ............. | 348/142 |
| 5,555,090 A * | 9/1996 | Schmutz | ....................... | 356/601 |
| 6,208,886 B1 * | 3/2001 | Alfano et al. | ................ | 600/473 |
| 6,549,288 B1 * | 4/2003 | Migdal et al. | ................ | 356/603 |
| 7,242,485 B2 * | 7/2007 | Akishiba | ....................... | 356/614 |
| 7,403,812 B2 * | 7/2008 | Rice et al. | ..................... | 600/473 |
| 7,782,470 B2 * | 8/2010 | Domenicali et al. | ........ | 356/614 |
| 2008/0200818 A1 * | 8/2008 | Determan et al. | ........... | 600/476 |
| 2008/0204697 A1 * | 8/2008 | Domenicali et al. | .............. | 356/2 |

* cited by examiner

*Primary Examiner* — Hoa Q Pham
(74) *Attorney, Agent, or Firm* — Cohen Pontani Lieberman & Pavane LLP (57) ABSTRACT

The invention provides for surface mapping of in-vivo imaging subjects using a single camera and an illuminator that projects a plurality of targets such as spots on the subject. By limiting the depth-of-field of the camera lens, or of the illuminator optics, or both, a spatial plane is defined in which the spots are most sharply in focus. Controlled displacement of this plane relative to the subject is achieved through movement of the mechanical stage on which a subject is placed; or through movement of the best-focus plane by adjustment of the camera, lens, or illuminator optics. Images are taken at several relative positions of the best-focus plane and the subject, and the height of individual points on the subject is determined through analysis of focus, given the known displacements. A mesh or other surface can be constructed from individual point locations, to provide a surface map of the subject. Accuracy of 0.5 mm can be readily attained for mice and similarly sized subjects.

23 Claims, 5 Drawing Sheets

SURFACE MEASUREMENT OF IN-VIVO SUBJECTS USING SPOT PROJECTOR

RELATED APPLICATIONS

This application claims priority from U.S. Provisional Patent Application Ser. No. 60/877,313 which was filed on Dec. 27, 2006.

BACKGROUND OF THE INVENTION

In-vivo imaging systems are commercially available for imaging small animals such as mice, such as the Maestro system from CRI Inc., (Woburn Mass.), and the IVIS system from Xenogen (Hopkinton, Mass.).

Motorized sample stages are widely used in optical imaging equipment, to permit loading multiple samples, or to permit selection of a sub-region of the sample for closer examination or measurement.

Design of lenses and lens assemblies is discussed in a variety of textbooks such as Modern Optical Engineering, Warren J. Smith, McGraw-Hill, $3^{rd}$ Edition (2000). This describes the primary aspects of a lens assembly, including entrance and exit pupils and principal plane locations, as well as the factors determining them. These may be calculated using ray-tracing programs such as Zemax from Zemax Development Corp. (Bellevue, Wash.).

The benefits of mapping the surface contours of objects to be studied by optical imaging, have been recognized in the field of in-vivo imaging. See for example, US Patent Published Application 20060268153 to Rice et. al. which describe use of structured light and photographic views to attain this goal.

Use of structured light methods to perform surface mapping can be costly since specialized illumination optics are required.

It is desirable to provide for surface mapping that uses elements already present in an in-vivo imaging system to the greatest extent, with minimal change or addition of components; and that it should not require costly or complicated optics or illumination system.

SUMMARY OF THE INVENTION

At the core of the invention is the recognition that best-focus algorithms can be used as a means of sample contour mapping for in-vivo imaging, and that these can be combined with a simple projector that produces a grid of spot targets on the subject. In some embodiments the rays that produce the spots have relatively short depth-of-field, compared to the depth of field of the imaging system. In this case the spot projection system defines the overall depth-of-field, and its best-focus plane is used for subject contour determination.

In other embodiments, the converse is true: the spot projector has relatively large depth of field compared with the imaging system, and the imaging system defines the overall depth-of-field and its best-focus plane is used for subject contour determination.

In some embodiments, an epi-illumination system is used, based on a selective reflector in front of the objective. For example, the spots may be projected from an optical system disposed to one side, and the rays reflect from a partially reflective mirror towards the subject; a portion of the light from the subject passes through the selective reflector to the imaging objective. The use of separate objectives for subject illumination and subject imaging provides some design flexibility. For example, the illumination objective may only need to operate well at a narrow range of wavelengths such as is used for contour map measurements, while the imaging objective may need to perform other measurements under additional constraints. Or, the two objectives may be operated at different numerical aperture in object space, to provide different depths-of-field, as discussed above.

In other embodiments, the same objective is used to illuminate the subject and to produce an image of it on the detector. For example, a selective reflector may be introduced near the image of the subject, producing a pair of spatially distinct image planes. The detector is placed at one of these planes, and a pinhole grid illuminator is placed at the other, and baffling is provided so that light from the illuminator does not reach the detector except via interaction with the subject. The placement of the detector and pinhole grid at their respective planes is either assured by mechanical tolerances, or it is checked and adjusted as necessary.

So in these embodiments the best-focus plane of the illumination spots is inherently registered with the best-focus plane for image forming at the detector. Note that this registration is not affected by refocusing the objective, nor by movement relative to the subject, nor by imaging deficiencies of the objective (though these may distort the best-focus plane to some other surface, or reduce the best-focus acuity). The two planes remain coincident, since they are equivalent planes in the optical system. Put another way, the illuminator and detector share a common best-focus surface in object space, at which the illuminator produces the smallest spot, and the imaging system detects spots with greatest acuity. The detector will see the sharpest image when the subject surface is in this plane, at a spot location. There is some improvement in instrumental sensitivity since both the distribution of the illumination pattern and the detection of the pattern are dropping off as the subject surface departs from the best-focus plane; the resulting contrast reduction with departure from best-focus height is the product of two terms, each of which degrades with height.

In yet other embodiments, the optical axes of the illumination and imaging systems are not coincident, but are offset in position or angle. Provided that the offset is not so great as to degrade the estimation of best-focus surface, this arrangement may be used, with an optional correction for geometrical distortion of the calculated height, if one is introduced by the offset.

As seen in the previous example, very little additional apparatus is required for practice of this invention, provided that an imaging system is already present. The additional elements can be as few as: a source of illumination, a pinhole grid, and a selective reflector that can be introduced into the system.

One benefit of the present invention is that it requires no special contrast, texture, or other special features to be present on the subject surface. The projection system provides a means for best-focus determination in any case.

Another benefit is that the system determines the best-focus height, or z-coordinate, at each of the spot (x, y) locations. Unlike a feature-based contour system, which relies upon subject features whose presence or location can vary from subject to subject, the spot (x, y) locations are determined by the illuminator, so are known in advance for all subjects. Further, the spot placement pattern is determined by the optical design of the illuminator. In many cases, this pattern can be chosen with great latitude, limited only by the spatial resolving power of the illuminator objective lens. So it is possible to obtain a contour map of (x, y, z) for the subject at nearly any desired set of (x, y) points. These points may form a Cartesian grid of evenly-spaced points in the (x, y)

plane, or they may form a different regular pattern of interest, or any pattern whatsoever within the limitations of the illuminator optics.

While the description so far has referred to spots, other illumination features could be used, such as small resolution targets or other contrast-bearing regions. What is essential is that they provide a pattern whose intersection with the subject provides a light pattern from which best-focus can be determined.

Several methods can be used to produce relative motion between the best focus plane and the subject. For example, in one embodiment a motorized stage is used to move the subject up and down by known amounts while it is at least partially within the field of view of the imaging system. It is not necessary to move the imaging or illumination system in this embodiment. Images are taken with the subject in each stage position. By analyzing the sharpness of focus for individual spots on the subject as the stage is moved to each position, it is possible to determine the height above the stage surface for each spot. By tracking sharpness measures for spots, using metrics such as the image volume of gradients or another measure of high-spatial frequency content, and interpolating for best-focus, one can determine spot z-location to within 0.5 mm while taking images at moderate intervals such as every 1 mm of stage height motion.

Alternatively, the subject may remain fixed while the imaging and/or illumination system moves and a similar process of spot focus is undertaken, with the same result that the best-focus configuration is noted for each spot, and the subject height at that spot is determined. This may involve moving the entire set of illumination and imaging optics; or it may involve adjusting portions of one or more of these subsystems.

In some embodiments, the imaging system has a long depth of focus and only the illuminator is moved. In alternative embodiments, the illuminator has a long depth of focus and only the imaging system is moved. In yet other embodiments, both the illuminator and the imager move relative to the subject, regardless of the relative depth-of-field of these two subsystems. In yet other systems, one or more of the objectives are adjusted to shift its focus, but all other components are fixed. Any arrangement may be used so long as it shifts the location of the best-focus plane relative to the subject by a known amount.

Typically, the spots are distributed across the surface of the subject, and form the reference points for depth measurements. A mesh can be constructed from a network of such features, and this mesh is an estimate of the actual subject contour.

The invention is normally practiced as part of the apparatus and method of operation of an in-vivo imaging system. This is especially favored when the imaging system provides the necessary imaging and stage apparatus already to perform other essential functions. However, the invention can be practiced on a separate apparatus, such as a separate imaging station on which the subject profile is obtained before or after another in-vivo imaging measurement of interest. The imaging measurement data may be combined with the contour information in order to interpret the results. For example, the in-vivo imaging apparatus and method may be used to obtain a fluorescence image or a set of multispectral fluorescence images. Or, it may be used to obtain an bioluminescent image of the subject. In either case, one obtains an image based on the location of chemical compounds within the subject, and the interaction of light with tissue as it propagates within the subject. Knowledge of the three-dimensional shape of the subject can be used as an input to models such as Monte-Carlo models or photon diffusion models, to obtain an improved estimate of the amount and location of chemical compounds within the subject.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like references denote similar elements throughout the several views.

DETAILED DESCRIPTION OF THE PRESENTLY PREFERRED EMBODIMENTS

In this discussion, technical terms have their normal meanings unless stated otherwise. "Subject" refers to an intact animal subject, including without limitation a mouse, rat, human, cat, dog, monkey, zebrafish, or any other creature for which it is desired to learn its surface contours. "Object" refers to a physical object, such as a subject, whereas "image" refers to an image formed by optics of some kind.

"Lens" means any type of lens or lens assembly, unless a more specific term is used. "Light" means light of any type whatsoever, including ultraviolet, visible, and infrared light. "Stage" means an apparatus for holding or supporting a subject. "Height" means a specified distance above the stage. Unless stated otherwise, the coordinate system is defined such that the Z axis is perpendicular to the stage surface, and its surface defines an X-Y coordinate plane. "Source" means a source of light, including without limitation an incandescent lamp, metal-halide lamp, mercury lamp, laser, light-emitting diode or array of same, electroluminescent emitter, or indeed any structure or arrangement that emits light in sufficient quantity to practice the invention.

"Spot" refers to a localized target used for best-focus determination. It may be a simple pinhole, or image of a pinhole; or it may be another target such as a compact bar grouping such as the groupings which appear in the US Air Force resolution target; or it may be a small star, cross, or radial pattern; or indeed it may be any structure from which a best-focus determination can be made when a subject is illuminated with this pattern.

The invention is best explained by relating specific embodiments. It will be understood, however, that this is done for ease and clarity of illustration, and that the invention can be practiced more broadly, or with different apparatus, without deviating from its spirit.

The invention has as its aim the determination of the surface contours of a subject. Commonly, this is a subject intended for measurement in an in-vivo imaging experiment such as a fluorescence or bioluminescence imaging experiment. However, the invention can be used to measure the surface contours of subjects for other uses as well.

Figure 1:
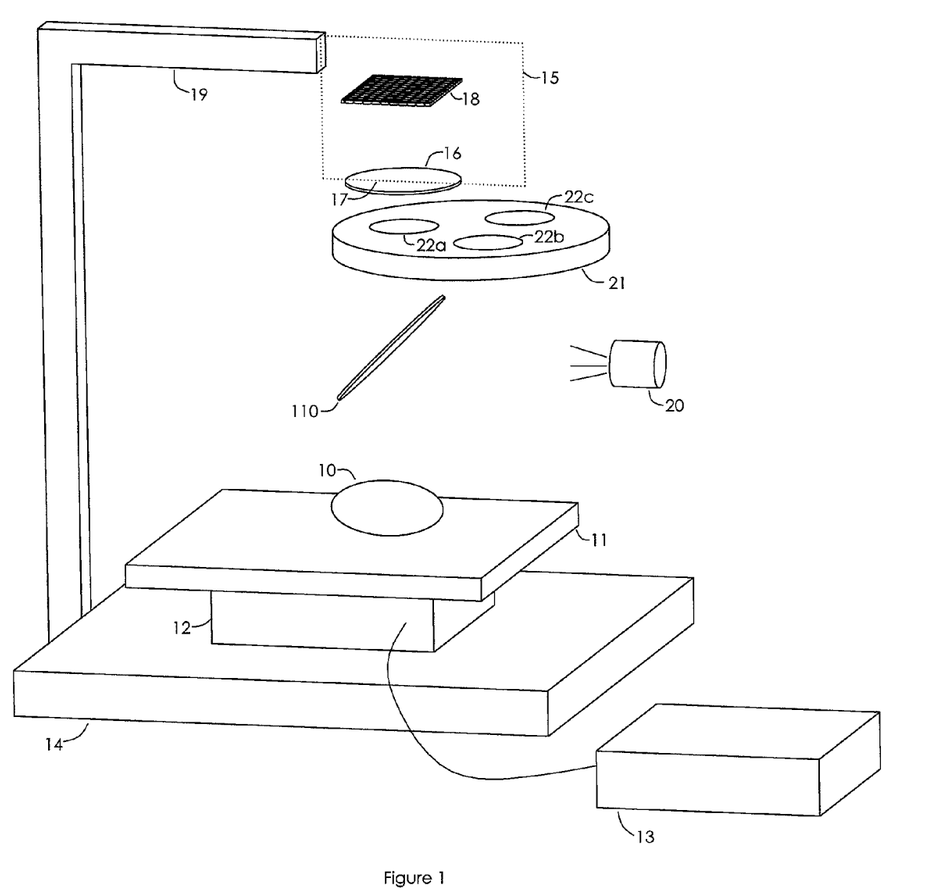
FIG. 1 is a schematic perspective view of an in-vivo imaging instrument according to the present invention.

FIG. 1 shows a schematic representation of an in-vivo imaging instrument suitable for practicing the invention. A subject 10 is placed on a stage 11 which is moveable in some embodiments by motion control elements 12 controlled by computer 13. The control elements are connected between the stage 11 and a chassis 14. An imaging system 15 includes an objective lens 16 having an entrance pupil 17 and a sensor 18, and is connected to the chassis 14 by a support member 19. Illumination source 20 illuminates the subject. Optional filter wheel 21 in front of the objective lens 16 selects filter 22a, 22b, or 22c to define a wavelength band or bands for the imaging measurement. A selective reflector 110 directs light from the illumination source 20 onto the subject 10. The subject may optionally be supported or surrounded by apparatus to provide a controlled temperature environment, or to restrain it against movement, or to deliver anesthesia, or combinations of these.

Figure 3:
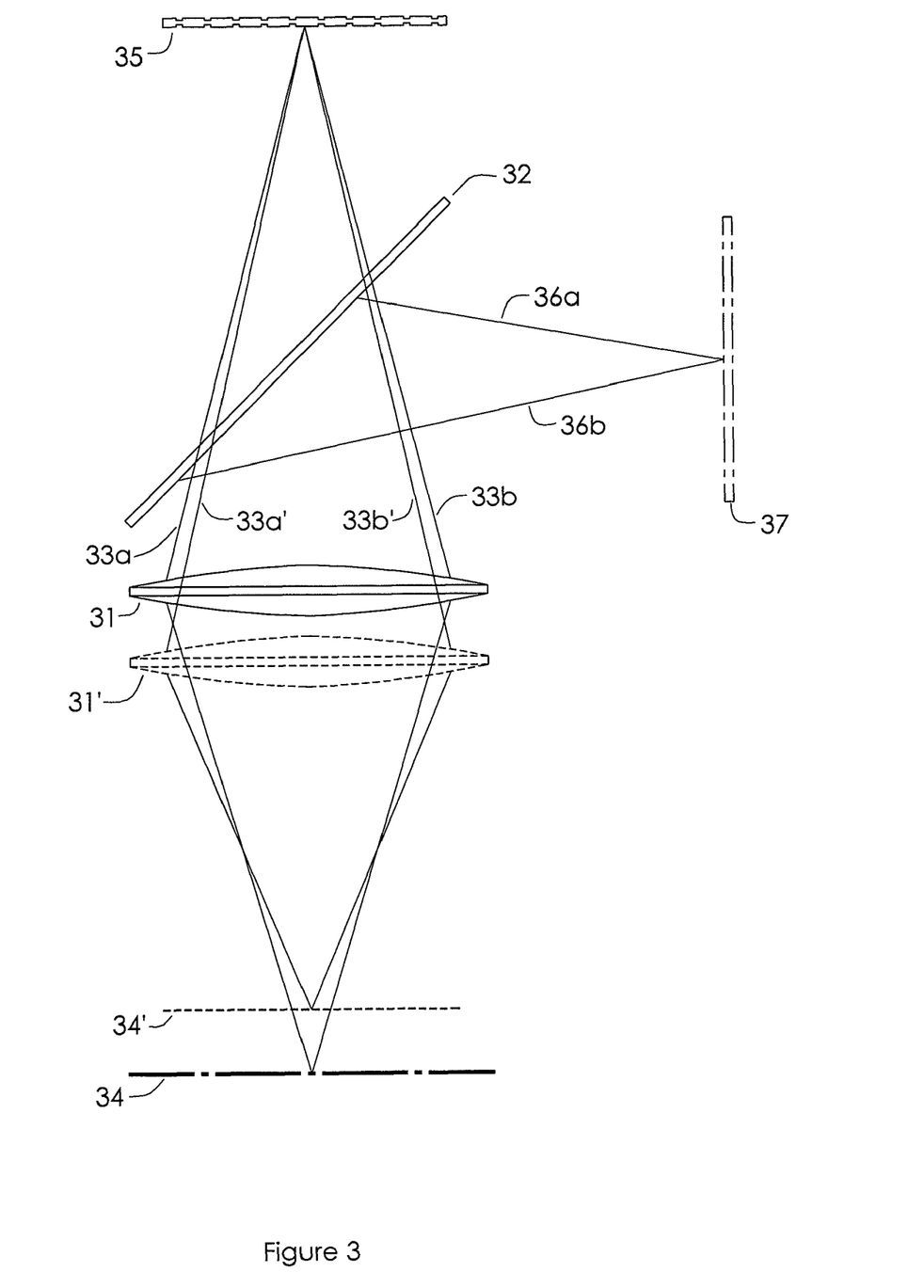
FIG. 3 is a schematic diagram of an optical system which may be used in the device of FIG. 1.

FIG. 3 shows a schematic diagram of an optical system for use in the device of FIG. 1 according to an embodiment where the illuminator and imaging system share a common objective 31. A selective reflector 32 divides the light rays 33a and 33b collected by the objective so a portion create an image of object plane 34 at the surface of detector 35, and a portion of rays 36a and 36b form an equivalent image at the surface of pinhole target 37 that is illuminated by light source 38. Equivalently, light from pinhole target 37 reflected by selective reflector 32 passes through objective 31 and forms an image of target 37 at object plane 34. When objective is placed in alternative position 31' the object plane moves to alternative position 34'.

Figure 4:
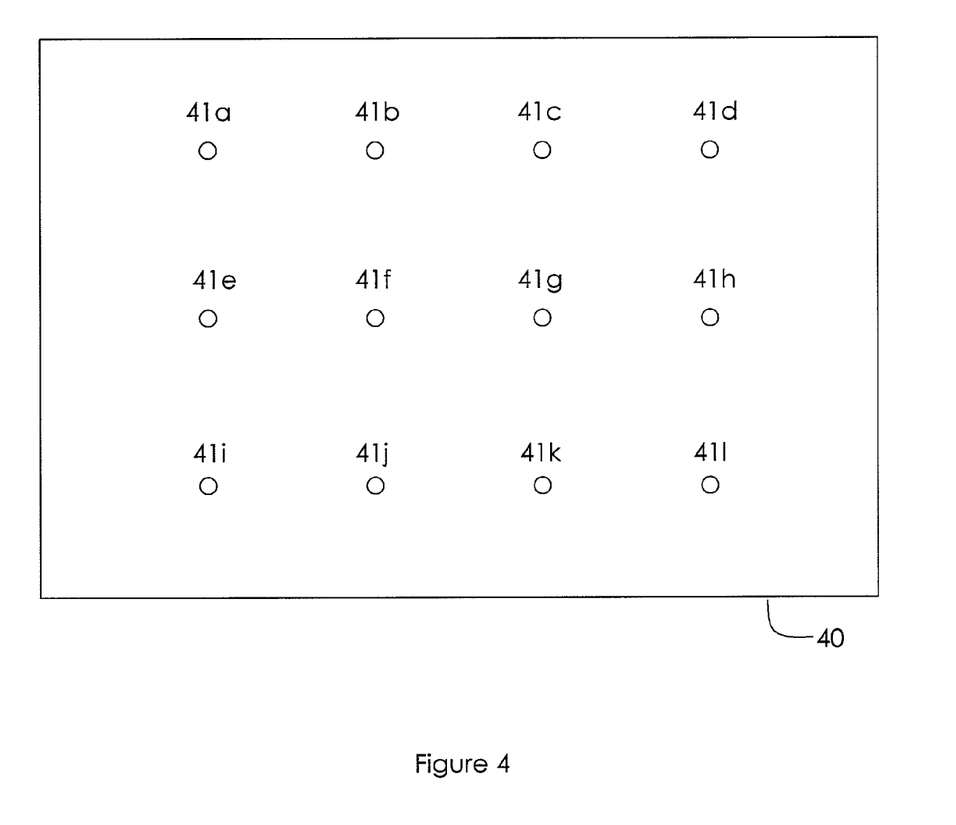
FIG. 4 is a plan view of a pinhole target for the device of FIG. 1.

FIG. 4 shows a plan view of a sample pinhole target 40 with holes 41a-41l arranged in a two-dimensional 3×4 grid. This pinhole target 40 may be used as the pinhole target 37 in the optical system of FIG. 3.

Figure 5:
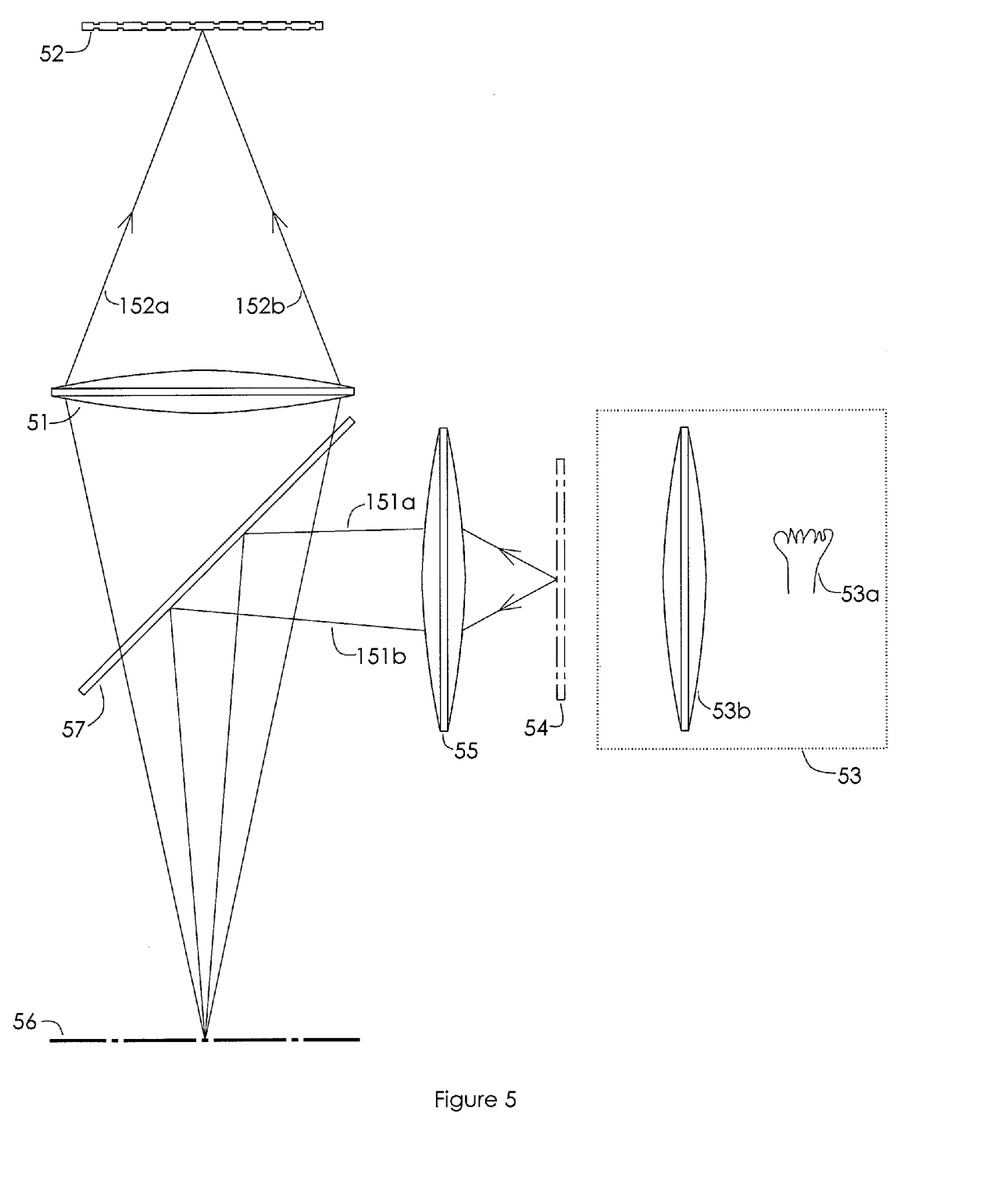
FIG. 5 is a schematic diagram of another optical system which may be used in the device of FIG. 1.

FIG. 5 shows a schematic diagram of another optical system for use in the device of FIG. 1 according to an embodiment where the illuminator and imaging system have separate objectives. Imaging objective 51 forms an image of plane 56 in object space at the surface of imaging detector 52. Light from source 53 passes through pinhole target 54 which is imaged by illuminator objective 55 and reflects off the surface of selective reflector 57 to form an image of the pinholes at plane 56.

The lens 16, 31, 51 is set to bring a selected object plane within the subject, to a focus at the imaging detector. A first image of the subject is recorded by the imaging system with the stage in a first position, and then the stage is moved by a known amount δz and a second image is recorded. For both images, the subject is illuminated with a plurality of spots, as described in detail below, and an estimate of focus is determined for the spots on the surface of the subject.

Since the goal is to map the contour of the subject, it will be understood that the subject spans a range of heights. Similarly, the lens has a finite range over which objects can be clearly distinguished, which is denoted its depth-of-field. This depends on the aperture and magnification, as is known in the optical art. The depth of field in object space is approximately given by $$DOF = 2S*F/M^2 \quad [1]$$

where S is the resolvable spot size of the detector, F is the working F/number of the objective, and M is the image:object magnification factor. Note that the working F/number is higher than the nominal F/number, when operating at finite conjugate ratios, as is known in the art of optical design.

It is often desirable to select an imaging system for which the depth-of-field is comparable to the contour height resolution that is sought, or larger. This enables the contour to be determined without an overly large number of images being taken. However, it is possible to practice the invention when the depth-of-field is finer than the contour height resolution being sought, though this may increase the number of images required.

For simplicity, the lens is treated in this discussion as if it were a perfect, thin lens element that obeys the paraxial lens approximation. This idealized lens assumption makes it easy to draw and understand optical diagrams, but such lenses do not exist in practice. One preferably will use a highly corrected lens such as the Micro-Nikkor AF60 D F/2.8 lens from Nikon (Melville, N.Y.), which is nearly perfect in its imaging properties and yields nearly-ideal performance. While this lens is exemplary of a high-quality lens, other lenses from other suppliers may be used provided that they have adequate imaging quality in terms of field of view, flatness of field, sharpness, and so on.

The minimum resolvable depth difference is an important figure-of-merit for a contour measurement system. Here we shall provide such an estimate for the invention in the case where the limiting angular resolution is that of a single pixel in the sensor. In this estimate, we use the thin-lens paraxial approximation where the principal planes and pupils are coincident with the lens itself and lens imaging properties are perfect. The latter condition can typically be attained with modern lens assemblies. To apply the results of this analysis to a real system, one may determine the actual locations of the pupils and principal planes of a lens using ray tracing programs or measurements. So these simplifications do not materially alter the result, compared to what can be attained in practice, or when a more detailed analysis is performed.

Modern scientific imaging sensors typically offer megapixel resolution, or higher. For example the Sony ICX-285 sensor has 1024×1392 resolution, meaning it is possible to discern 1000 spots or more, in any direction. The QImaging Retiga EXi from QImaging (Burnaby, British Columbia, Canada) is an example of a camera using this sensor. Similarly, the Texas Instruments Impactron EMCCD offers 1004× 1002 pixel resolution, and is used in the iXon EM DV885-LC camera from Andor Technology (Belfast, Northern Ireland). Both of these cameras offer very high sensitivity and are suitable for scientific grade imaging.

There is also an illumination system which is used for purposes of surface contour measurement. This system projects a pattern of sharpness spots on the subject, and it produces the sharpest spot pattern on the subject at a surface that is substantially coincident with the best-focus plane for the imaging system; or, in the alternative, the surface lies within the depth-of-field for the illumination system or of the imaging system, whichever is greater.

One approach is to create the pattern by creating a spatially extensive light source which is spatially patterned by means of a mask such as a patterned metal film or sheet. For example, one may use a chrome surface which is patterned using photolithography, to generate a pattern of more transparent and less transparent regions. This can be a suitable mask.

It is often beneficial to practice the present invention together with, or as part of, a high-performance measurement system such as an in-vivo fluorescence or luminescence measurement system. In such cases, an imaging sensor may already be present for purposes of making other measurements as in the device of FIG. 1. When this is the case, it can be beneficial to use that existing imaging sensor for practicing this invention. However, this is not essential, and it is possible to use a separate imaging sensor, or a lower-performance imaging sensor, for practicing this invention. All that is important is that the sensor have sufficient size and resolution to provide the necessary images. It can be possible to use CMOS imaging sensors or other low-cost imaging sensors to practice the invention in cases where the sensor is not used for other measurements or subjected to other constraints.

One may consider some practical cases of interest. Suppose one uses a 50 mm lens and operates it at a 2:1 conjugate ratio, to produce a half-size image of the subject. The lens is an F/2 model but because it is at 2:1 conjugate ratio, the effective F/number is 3. The image is measured using a Kodak KAF-4202 imaging sensor (Kodak Image Sensor Solutions, Rochester N.Y.). This yields an 18 mm square image of the subject, with 2000×2000 pixel resolution. The subject is a mouse, which has a maximum height of 20 mm, and the lens is focused at the midpoint of the mouse.

For this system, the depth-of-field is given by $$DOF = 2*9\mu*3*2^2 = 216 \text{ microns} \qquad [2]$$

If the same arrangement is operated at F/6, the DOF is 432 microns. In an alternative embodiment, the mouse is imaged at a 4:1 conjugate ratio, to view a 72×72 mm sample region. It may be analyzed using the same equations and methodology. We tabulate the principal quantities for these cases as follows:

TABLE 1

Depth resolution for sample instrument used at various magnifications.

| Mag | Working distance | Sample region | F/# (nom) | F/# (wkg) | Spot size at sensor | DOF | Steps | Δz |
|---|---|---|---|---|---|---|---|---|
| 2:1 | 150 mm | 36 mm × 36 mm | 2 | 3 | 9μ | 0.22 mm | 40 | 0.25 mm |
| 2:1 | 150 mm | 36 mm × 36 mm | 4 | 6 | 9μ | 0.43 mm | 40 | 0.25 mm |
| 4:1 | 250 mm | 72 mm × 72 mm | 2 | 2.5 | 9μ | 0.72 mm | 20 | 0.50 mm |
| 4:1 | 250 mm | 72 mm × 72 mm | 4 | 5 | 9μ | 1.44 mm | 20 | 0.72 mm |

In other instruments, the sensor size and pixel resolution may be different, but the principle of operation, and of estimating the degree of depth resolution that can be attained, is similar.

The example above considers the case where the stage is moved by an amount of 0.5 mm for the high-resolution maps, and 1 mm for the low resolution maps. However, other movements may be used according to the need at hand. The resolution and step size will depend on the requirement at hand for the subject and the degree of accuracy sought in the contour map.

The overall process consists of the measurements just described, along with a process for data analysis. In any practical system, the overall contour measurement is done in an automated manner, using computer analysis of the various images. So, it is necessary to analyze the images; determine the subject height at a plurality of locations on the subject surface; and construct a contour from the height values.

The data analysis involves automatic assignment of a sharpness and location to each spot in each image; automatic correlation of which spot in each image corresponds to the same spot in other images; and construction of the contour from the mesh of spots, once the height is determined for each one.

Note that the apparent location of any off-center spot will change slightly as the stage is moved in Z unless the lens is telecentric in object space. This can yield additional information about the subject feature location in some cases. However, in all cases it is necessary to recognize this effect, and to process spot images from successive images so the image analysis is not affected in unwanted ways. For example, the exact pixels corresponding to a given spot may change according to stage height, which must be accommodated by the exact focus estimation algorithm used.

A survey of methods for determination of best-focus is presented by Sun et. al. in "Autofocusing in computer microscopy: Selecting the optimal focus algorithm", Yu Sun, Stefan Duthaler, Bradley Nelson, Microscopy Research and Technique 65, pp. 139-149, Wiley-Interscience (online, www.interscience.wiley.com) (2004). The 18 algorithms listed therein include gradient methods, Laplace methods, variance and autocorrelation methods, and statistical measures of the pixel values. Favored methods include normalized variance and standard-deviation based correlation, but others can be used as well. In the manner taught by that article, which is included in its entirety in this application, it is possible to select an algorithm based on its performance for actual samples, using criteria such as accuracy, range, false maxima, peak width, and noise level to rank candidate algorithms. While that article describes focus algorithm performance for purposes of computerized focusing of a microscope on a nominally planar sample, the same principles apply in using optimum focus algorithms in the context of the present invention, where the goal is to assess best-focus of images or subregions of images of a three-dimensional subject in order to estimate what height corresponds most nearly to the image region or subregion.

Figure 2:
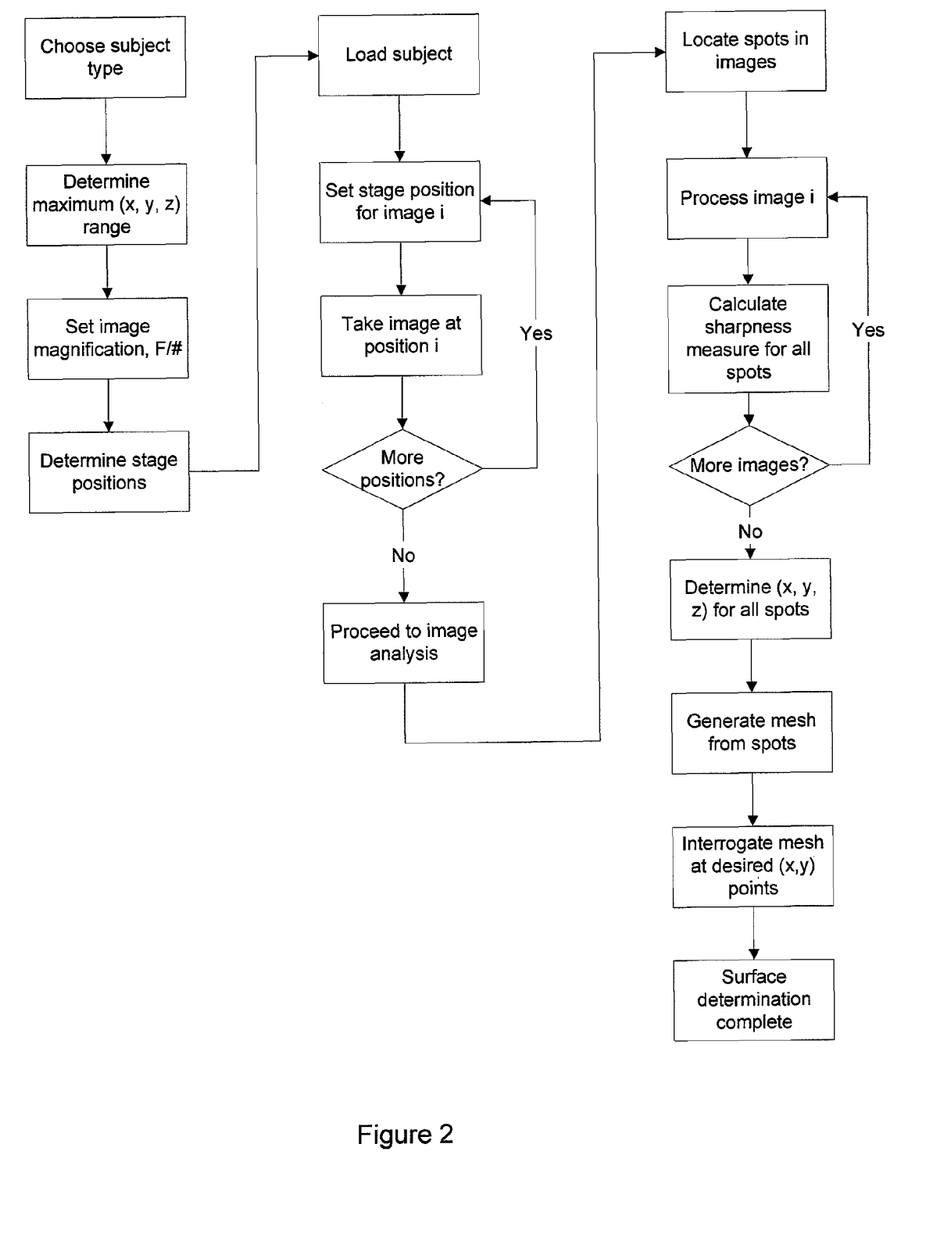
FIG. 2 is a flow diagram showing the steps for contour determination according to a first embodiment using the device of FIG. 1.

The overall measurement process is shown in FIG. 2. A subject is loaded, the stage location is chosen, the stage is set to that position, a resolution is chosen and the instrument parameters are chosen, including F/number, magnification, and Z step size; the image is taken, and the process is repeated according to the flowchart logic, until all subject regions of interest have been imaged in the various stage positions. Then, spots are identified in each image, and image coordinates assigned to each. The correspondence between spots in different images is determined. A focus sharpness estimate is determined for each spot in the region surrounding its best-focus height, from which the height at the spot is determined. The x and y coordinate of each feature is also determined, relative to a coordinate system, and knowing the position of the lens entrance pupil. Each feature is added to a list of spots and 3-dimensional locations to form a list of spots. From the spot mesh, a contour surface is generated.

It is not necessary that equal sized steps be used for the contour measurement. For example, one may use smaller steps when mapping a height region of the subject for which improved resolution is sought, and then change to larger steps when mapping a height region of the subject for which coarse resolution is sufficient; or vice versa. Similarly, the F/number of the lens may be changed within the course of the measurement to change the depth-of-field used for different sub-ranges of the overall height range being measured.

However, the invention is not limited to use in fluorescent imaging modes. Ordinary reflected light imaging can also be used if that is preferred, and if it yields features that can be detected for a given subject. Indeed, any imaging mode may be used that provides feature location data, and the choice can be made based on factors such as what imaging modes are available for a given set of apparatus; what types of subjects are to be viewed and what features are present; and speed of image acquisition.

It is possible to provide for lateral stage motion, and measure the subject twice: once when it is in a first location; then again when it has been shifted by half the inter-spot distance. By combining the two measurements one obtains a contour measurement with twice the density of points. This method can be done with a variety of shift distances, and numbers of measurements. For example, one may perform a total of four measurements, corresponding to a first location; a location shifted by ($\delta$, 0); at a location shifted by (0, $\delta$); and at a location shifted by ($\delta$, $\delta$); where the spot pattern is a Cartesian grid of spots equally spaced by $2\delta$ in x and y. The information from the four measurements may be combined to provide a surface measurement that is twice as dense in both dimensions as a single measurement would be. Other schemes of this type may be performed, according to the needs of the task at hand.

In some cases it may be preferred to provide a separate station for the contour measurement, rather than to make this part of a larger instrument system. This may be done because the imaging sensor in the larger instrument system is not suitable for the contour measurements; or because it is desired to provide the contour measurement as an accessory to an existing system; or to provide increased temporal throughput for the workstation; or for a variety of reasons. In any case, it is possible to perform the contour measurement before or after another measurement of interest; and then to combine the contour information with the results of the other measurement to arrive at a more complete understanding of the subject.

While it is expected that the invention is normally practiced on subjects which are anaesthetized or otherwise immobilized, the subject may still exhibit slight movement due to respiration and circulation functions. If it is desired, one may synchronize the image acquisition with subject breathing or heartbeat to reduce the effect of these factors on the measurement. Alternatively, several images can be taken which span the period of the movement, from which an improved estimate of position can be obtained by taking a mean value, or in the case of a repetitive movement, interpreting the images to determine which position corresponds to a specific state in the movement cycle.

Thus, while the invention has been described by use of specific, other embodiments can be employed without deviating from the invention. For example, one may employ a wide range of imaging sensors and lenses, consistent with the need to yield a suitable image of the subject. Similarly, any stage may be used that can move the subject over the required range of positions. Turning to the data analysis and derivation of a contour surface, there are many ways to exploit the core focus estimation approach that the invention provides, and the methods shown herein should be considered a non-limiting guide to how this can be accomplished. Alternative approaches can be used, such as lookup tables, numerical calculations, and so on, provided that the result is that a height estimate is determined from the apparent sharpness of focus of a feature in two or more images taken from different positions relative to the subject. Accordingly, it is understood that the scope of the invention is limited only be the attached claims, and not by the specific examples and embodiments.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for determining a contour of a subject using an in-vivo measurement system having a stage supporting the subject, control elements connected to a controller, and an imaging system having an optical axis, the method comprising the steps of:
    generating, by a projector, rays incident on the subject supported on the stage of the in-vivo measurement system for producing a light pattern on the subject, wherein the rays incident on the subject for producing the light pattern are directed substantially in the direction of the optical axis of the imaging system of the in-vivo measurement system;
    incrementally moving, by the control elements, at least one of the stage and the object plane of the imaging system to a plurality of positions substantially in a direction of an optical axis of the imaging system;
    taking, by the imaging system, images of the subject at each of the stage positions;
    analyzing, by the controller, sharpness of focus for each of a plurality of points in the light pattern to determine the heights of each of the plurality of points; and
    constructing, by the controller, a contour of the subject from the height values.

2. The method of claim 1, wherein the rays that produce the light pattern have a depth of field that is shorter than the depth of field of the imaging system.

3. The method of claim 1, wherein the rays that produce the light pattern have a depth of field that is larger than the depth of field of the imaging system.

4. The method of claim 1, wherein said step of constructing comprises constructing a mesh from a network of the individual height values as an estimate of an actual contour of the subject.

5. The method of claim 1, wherein the step of generating comprises reflecting the rays from a partially reflective mirror toward the subject.

6. The method of claim 1, wherein the subject is a mouse or a rat.

7. The method of claim 1, wherein said step of taking images is performed using reflected light.

8. The method of claim 1, further comprising the step of taking an in-vivo image of the subject for an in-vivo imaging experiment and analyzing the in-vivo image using the constructed contour.

9. The method of claim 8, wherein the in-vivo image is obtained using fluorescence or bioluminescence emitted from the subject.

10. The method of claim 9, wherein the step of taking images of the subject at each of the positions is performed using reflected ambient light.

11. The method of claim 1, wherein the pattern of light is a grid of spot targets.

12. An in-vivo imaging system, comprising:
a stage for supporting a subject in the in-vivo measurement system;
an imaging system of the in-vivo measurement system having an optical axis;
a projector configured to generate rays incident on the subject for producing a light pattern on the subject, the rays incident on the subject directed substantially in the direction of the optical axis of the imaging system; and
control elements connected to a controller, the control elements configured to move at least one of the stage and imaging system toward or away from the other of the stage and imaging system, said controller and imaging system configured to determine a best-focus height of a plurality of points in the light pattern by analyzing sharpness of focus for each of the plurality of points, whereby a contour of the subject is determinable from the best-focus heights.

13. The in-vivo imaging system of claim 12, wherein said controller stores an executable program for determining the contour of the subject, the program comprising the executable steps of:
activating said projector to produce the light pattern on the subject supported on said stage;
incrementally moving, by said control elements, at least one of said stage and said imaging system to a plurality of positions such that said stage and said imaging system are moved toward or away from each other;
taking, by said imaging system, images at each of the stage positions;
analyzing, by said controller, sharpness of focus for each of the plurality of points in the light pattern to determine the best-focus heights of each of the plurality of points; and
constructing, by the controller, the contour of the subject from the best-focus height values.

14. The in-vivo imaging system of claim 13, wherein the program further comprises the executable step of taking an in-vivo image of the subject for an in-vivo imaging experiment and analyzing the in-vivo image using the constructed contour.

15. The in-vivo imaging system of claim 14, wherein the in-vivo image is obtained using fluorescence or bioluminescence emitted from the subject.

16. The in-vivo imaging system of claim 15, wherein the step of taking images of the subject at each of the positions is performed using reflected ambient light.

17. The in-vivo imaging system of claim 12, wherein said projector has an illumination device and a grid for forming the light pattern.

18. The in-vivo imaging system of claim 17, wherein the grid is a pinhole grid and the light pattern produced by said projector is a grid of spot targets.

19. The in-vivo imaging system of claim 12, wherein said projector further comprises an illumination objective and said imaging system comprises an imaging objective.

20. The in-vivo imaging system of claim 19, wherein the illumination objective produces a depth of field of the grid of spot targets that is shorter than the depth of field of the imaging objective of the imaging system.

21. The in-vivo imaging system of claim 19, wherein the illumination objective produces a depth of field of the grid of spot targets that is larger than the depth of field of the imaging objective of the imaging system.

22. The in-vivo imaging system of claim 12, further comprising a selective reflector for reflecting the rays toward the subject.

23. The in-vivo imaging system of claim 22, wherein the projector is disposed to one side of the imaging system and said stage.

* * * * *